United States Patent [19]
Akiyama et al.

[11] Patent Number: 5,361,030
[45] Date of Patent: Nov. 1, 1994

[54] LEAK DETECTOR FOR ELECTRO-MAGNETIC INDUCTION-TYPE CONDUCTIVITY METER

[75] Inventors: Shigeyuki Akiyama; Hiroo Matsumoto, both of Miyanohigashi, Japan

[73] Assignee: Horiba, Ltd., Kyoto, Japan

[21] Appl. No.: 928,987

[22] Filed: Aug. 12, 1992

Related U.S. Application Data

[63] Continuation-in-part of Ser. No. 781,712, Oct. 22, 1991, Pat. No. 5,252,925.

Foreign Application Priority Data

Aug. 14, 1991 [JP] Japan .................... 3-072271[U]

[51] Int. Cl.$^5$ .................. G01N 27/28; G01N 27/02
[52] U.S. Cl. .................... 324/445; 324/450
[58] Field of Search ............ 324/439, 445, 450, 204, 324/693, 724, 219, 220, 239; 340/604, 605; 174/11 R

[56] References Cited

U.S. PATENT DOCUMENTS

| | | | |
|---|---|---|---|
| 3,404,336 | 10/1968 | Rosenthal | 324/445 |
| 3,662,367 | 5/1972 | De Veau, Jr. et al. | 340/605 |
| 3,721,970 | 3/1973 | Niemoth | 340/605 |
| 4,029,889 | 5/1977 | Mizuochi | 174/11 R |
| 4,197,531 | 4/1980 | Wentworth, Jr. | 340/605 |
| 4,527,804 | 7/1985 | Spencer | 174/11 R |
| 4,896,527 | 1/1990 | Akiba | 340/605 |
| 5,077,525 | 12/1991 | West | 324/204 |

*Primary Examiner*—Maura K. Regan
*Attorney, Agent, or Firm*—Price, Gess & Ubell

[57] ABSTRACT

An improved detector assembly of an electro-magnetic conduction-type conductivity meter includes a plastic housing member having a liquid sample flow path extending therethrough. An excitation transformer is mounted in a cavity of the housing member along with the detection transformer for respectively inducing a current flow and detecting a current flow in the liquid sample flow path. A porous electrode is positioned adjacent one of the transformers and insulated by hydrophilic paper so that the entrance of any fluid within the cavity can be detected.

6 Claims, 4 Drawing Sheets

LEAK DETECTOR FOR ELECTRO-MAGNETIC INDUCTION-TYPE CONDUCTIVITY METER

RELATED APPLICATIONS

This is a continuation-in-part application of U.S. patent application Ser. No. 07/781,712 now Pat. No. 5,252,925 filed on Oct. 22, 1991, for a DETECTOR ASSEMBLY FOR AN ELECTROMAGNETIC INDUCTION-TYPE CONDUCTIVITY METER.

BACKGROUND OF THE INVENTION

2. Field of the Invention

The present invention relates to an electro-magnetic induction-type conductivity meter for measuring the electric conductivity of a sample liquid wherein electric current is induced to pass through a liquid sample by electro-magnetic induction and detected by a detector coil to measure the conductivity of a sample. More particularly, the invention relates to a compact leak detector for monitoring the performance of the conductivity meter.

2. Description of Related Art

Electro-magnetic induction-type conductivity meters having a transformer portion consisting of a circular excited coil and a detecting coil extending about a passage of a sample liquid have been known. Meter of this configuration have been formed from a plastic resin casing with sample liquid being transported through the casing. Such a meter has usually been provided with a flange and a holder for mounting a detector element at a midway position relative to a pipeline in order to measure the electric conductivity of a liquid, such as a sample liquid flowing through the pipeline.

There have been efforts to make the casing or housing of superior resins with regard to the characteristics of electric installation and corrosion resistance to the sample liquid. Casings have been made of hard vinyl chloride, polypropylene, polyfluorovinylidene, or Teflon (trade name). Problems have occurred, however, in the production of such casings made of resins in that the wall thicknesses can be irregular. The transformer portion that is to interact with the sample liquid usually has a relatively thin wall construction and in a case where this portion is welded to a relatively thick wall portion, a structural strain can be generated. Over the life of the instrument, frequent contact with a sample liquid will occur and the resins can be damaged or cracked, for example, due to the temperature change of the sample liquid, thereby allowing the sample liquid to enter into the inside of the casing. As a result, the coil of the transformer portion can become corroded. Additionally, the measurement can be affected by the egress of liquid into the transformer portion and eventually the coil of the transformer portion will become corroded, and the conductivity meter will become inoperative. The conventional electro-magnetic induction-type conductivity meters have not taken into account an entrance of the sample liquid into a resin case and accordingly, such a malfunction has not been able to be detected until the coil is actually short-circuited.

An additional problem can occur in not only the metallic transformer case housing and the coil will become corroded and the conductivity meter will be damaged, but further this corrosion can then migrate into the sample liquid and can contaminate the liquid. For example, if a corrosive liquid, such as hydrofluoric acid, HF, is being measured, this HF is highly corrosive and will interact with the metallic transformer case housing to become contaminated with metallic ions, such as iron, zinc, chromium, and cobalt. Accordingly, there is still a demand in the prior art to provide an improved electro-magnetic induction-type conductivity meter.

SUMMARY OF THE INVENTION

The present invention is designed to address the problems mentioned above by providing a leak detector assembly of a compact configuration that is capable of an early detection of the entrance of any sample liquid into the inside of the conductivity meter casing. Thus, leaking resulting, for example, from a cracking of the case of a resin casing, can be immediately detected with the present invention.

A detector assembly of an electro-magnetic induction-type conductivity meter having a plastic material housing member with an excitation coil extending about a liquid sample flow path and a detection coil extending about the liquid sample flow path is further provided with an electrode member formed of a porous electrically conductive sheet on an outer surface of the transformer portion with a hydrophilic insulating paper to enable a detection of the entrance of any sample liquid within the casing. The entrance of the liquid will affect the electric conductivity between the electrode and the transformer portion which can excite an appropriately signal alarm. During the normal operation, when the resilient casing remains intact, sample liquid cannot enter into the inside of the casing and no electric conductivity is provided between the electrode and the transformer portion. However, if sample liquid enters, for example, through a crack in the casing, the sample liquid will enter the casing and will pass through the porous electrically conductive sheet electrode to make the hydrophilic insulating paper wet. As a result, the electric conductivity will be slightly generated between the electrode and the transformer portion. This condition can be detected by monitoring the value of any electric current flowing between the electrode and the transformer portion or any variance in the value of a resistance between the electrode and the transformer portion.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

Figure 1:
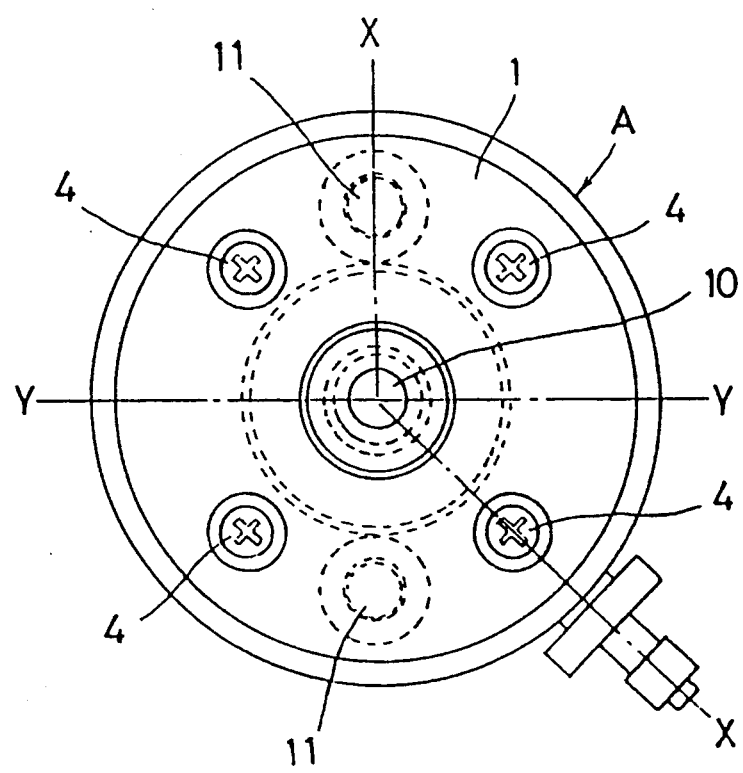
FIG. 1 is a plan view showing one example of a detector assembly of an electro-magnetic induction-type conductivity meter.

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved leak detector for an electromagnetic induction-type conductivity meter.

Referring to the preferred embodiment of FIGS. 1 through 4, a detector assembly for an electro-magnetic induction-type conductivity meter according to the present invention is disclosed. The detecting portion A has a housing or case 1 made from injection-molded resins and bifurcated into two block-shaped case members 2 and 3 that can be removably connected to each other by screw fasteners 4. The resins that are selected are generally superior in electric insulation and corrosion resistance and can include resins, such as hard vinyl chloride, polypropylene, polyflurovinylidene, or Teflon (trade name). The lower casing member 3 includes a male coupling tube providing a portion of a sample liquid passage 10. This convex coupling tube 5 can engage a female concave portion formed in the upper case member 2. Bores or holes 8 and 9 have respective openings 6 and 7 and are formed in a circular central portion of the upper and lower case members 2 and 3 to provide a linear communication with each other when the upper and lower casing members are integrated together, thereby forming a sample liquid passageway 10. In addition, two outer circumferential passageways 11 having a letter-shaped construction are also provided to create a bypass sample passageway 11 to extend about the excitation coil 17 and the detecting coil 18. A sealing ring member 12 is positioned between the upper and lower case members 2 and 3 and exterior male coupling projections 13 are positioned at either end of the respective upper and lower case members 2 and 3 and are of such a configuration to enable a coupling in a pipeline through which the sample liquid flows. A ring-like cavity 14 in the lower casing member 3 is of a configuration to receive the coil members so that a circular excited coil 17 and circular detecting coil 18 with a circular cone wrapped with wire coils can be housed in a metallic casing 15 and a metallic case 16, respectively.

Figure 2:
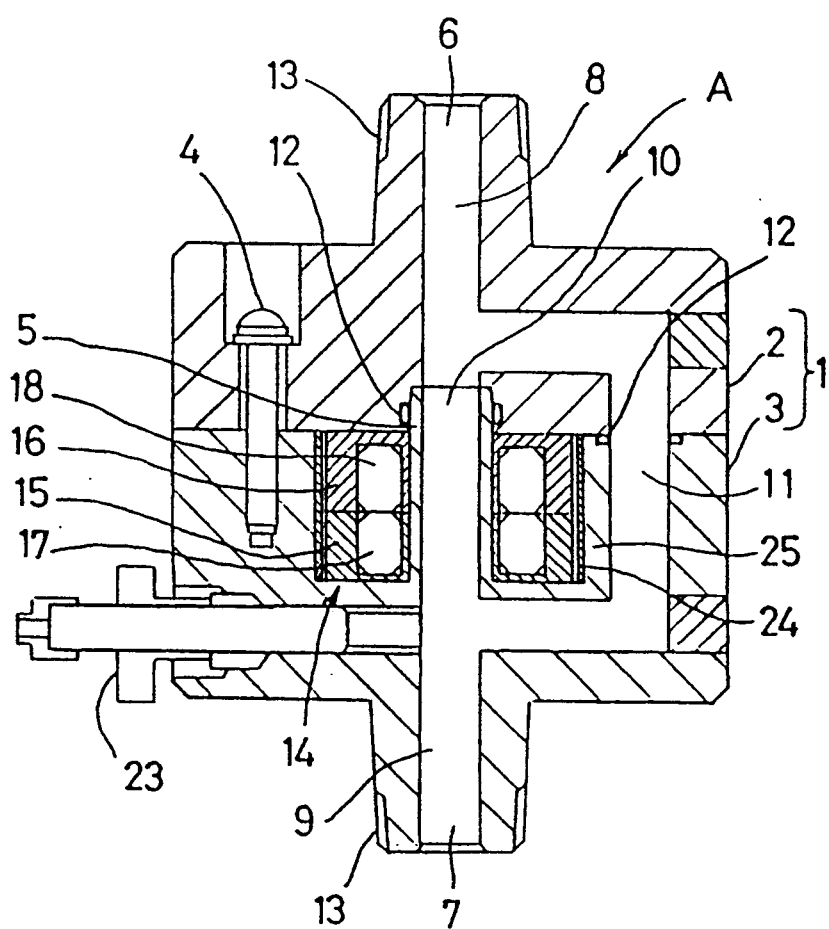
FIG. 2 is a longitudinal cross-sectional view of FIG. 1 taken along the line X—X thereof.
Figure 3:
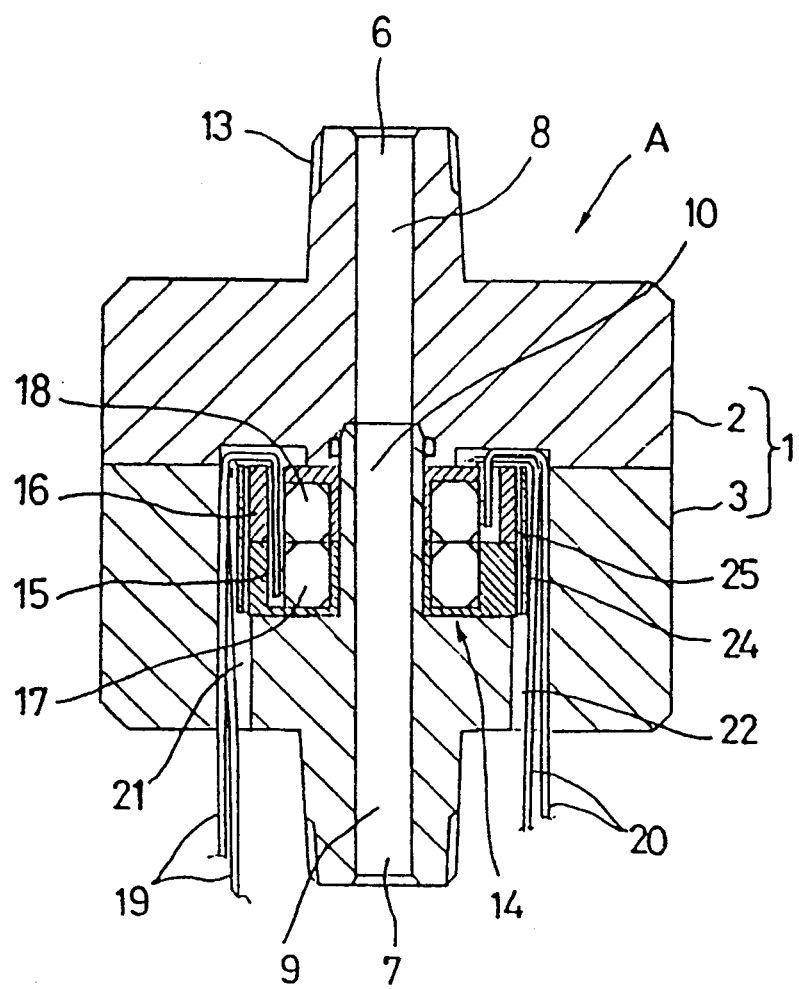
FIG. 3 is another longitudinal cross-sectional view of FIG. 1 taken along the sectional line Y—Y thereof.

As can be seen from FIG. 2, the respective excitation coil 17 and detection coil 18 are positioned to encircle the sample liquid passageway 10 and in turn be encircled by the bypass passageway 11. Lead wires 19 and 20 are respectively connected with the excitation coil 17 and the detection coil 18. The respective lead wires 19 and 20 extend through relatively fine or small holes 21 and 22, shown in FIG. 3, for appropriate connection with a power source (not shown).

Further specifics of the detector assembly can be seen in the co-pending parent application Ser. No. 07/781,712, which is incorporated herein to supplement the present disclosure material.

Referring to FIG. 2, a temperature sensor 23 having a sensor portion in communication with the sample liquid passageway 10 can be inserted in the lower case member 3. By measuring the temperature of the sample liquid with the temperature sensor 23, the electric conductivity can be measured to a high accuracy by correcting for any temperature changes in the sample liquid. As can be appreciated, the present invention is operative without providing such a temperature sensor and, in fact, when the sample liquid is kept at a relatively constant temperature by means of a thermostatic oven or the like, it is not necessary to include a temperature sensor to provide high accuracy.

There is a desire to address the leak problem while maintaining a very compact configuration. Thus, a minimum of space should be used for any leak sensor.

Figure 4:
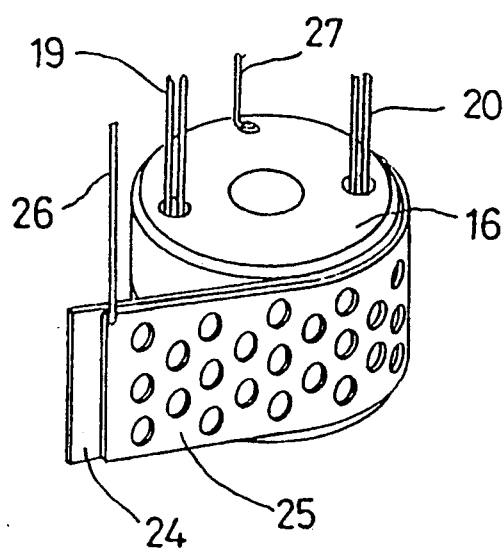
FIG. 4 is a perspective view showing an arrangement of the leak detecting electrode.

Referring to FIG. 4, the electrode sensor 25 of the present invention comprises an elongated thin porous electrically conducive sheet as appropriately mounted on the exterior surface of the transformer portion 14 and segregated from the transformer portion by an elongated belt-shaped hydrophilic insulating paper 24. The electrode sensor 25 can have a series of bores or circular holes. If the sample liquid enters inside the casing 1, the insulating paper 24 will receive the sample liquid and will effect the electrical relationship between the electrode 25 and the transformer portion 14, such as the electric conductibility. The hydrophilic insulating paper 24 is tightly wound around the outer side circumference surface of the respective excitation coil 17 and the detection coil 18, and then the belt-shaped electrode 25 that is formed of a porous electrically conductive sheet is tightly wound around the outer side of the hydrophilic insulating paper 24. As can be appreciated, the electrode 25 can be formed to be a thin metal foil, a carbon containing fiber sheet or a thin sheet of a carbon containing electrically conductive film. Preferably the electrode 25 is formed of a material that is superior in chemical resistance, at least relative to the type of sample liquid to be measured.

In addition, the hydrophilic insulating paper 24 should have a thickness capable of maintaining an insulation characteristic between the excitation coil 17 and the detecting coil 18. A lead wire 26 can be connected with the electrode 25, while a lead wire 27 is connected with the detection transformer 18. These respective lead wires 26 and 27 are connected through a detection circuit (not shown).

In operation, the detecting portion A having the above described construction can be connected midway of a pipeline (not shown) by coupling the pipeline with the coupling projecting portions 13. The sample liquid flowing through the pipeline will flow into the inside of the sample liquid passageway 10 through the opening 7. The sample liquid is further divided into the sample liquid passageway 10 and the outer circumferential passageway 11 to extend through the central portion and outer circumferential portions of the excitation coil 17 and the detecting coil 18. In operation, an induction current can be generated depending upon the electric conductivity of the electrolytes in the sample liquid from the excitation coil 17 and the electric conductivity of the sample liquid will be measured by detecting the induction current by means of the detection coil 18. The sample liquid flowing through respective sample liquid passageway 10 and the outer circumferential passageway 11 is then discharged through the opening 6.

In normal operation, the resin casing 1 remains intact and the sample liquid does not enter into the inside of this housing. Accordingly, no electric conductivity is produced between the electrode 25 and the transformer portion 14. If, for example, the integrity of the casing 1 is compromised, such as being cracked, the sample liquid will enter into the casing 1 to pass through the porous electrically conductive sheet electrode 25, to thereby make the hydrophilic insulating paper 24 wet. As a result of this liquid, the electric conductibility will be altered between the electrode 25 and the transformer portion 14. An electric signal can be generated when induction current of a certain value flows between the electrode 25 and the transformer portion 14, and this can be used as an input detection circuit (not shown), which can provide or display an alarm to the operator.

Although the electrode 25 as shown in FIG. 4, is adapted to cover the entire side portion of the transformer portion 14, it can be altered to selectively cover the welded portion in the thin wall portion having a reduced mechanical strength, since this is basically a weak point of the casing.

Figure 5:
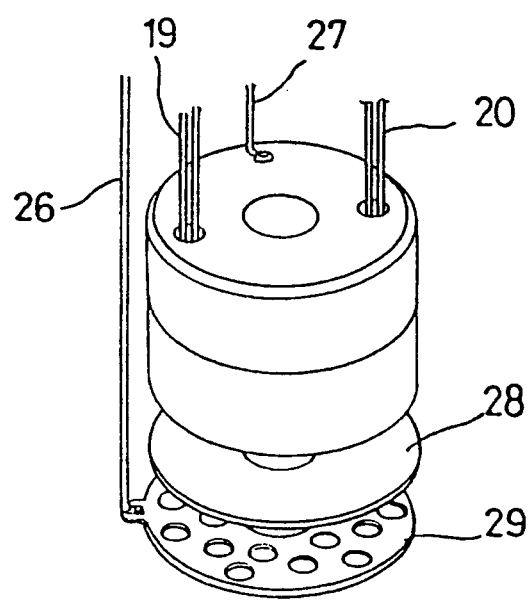
FIG. 5 is a perspective view showing a second embodiment of a leak detecting electrode of the present invention.

Another preferred embodiment of the present invention is disclosed in FIG. 5, wherein a disc-shaped or circular electrode 29 is formed on the bottom surface of the transformer portion 14 and is segregated from the transformer portion 14 through a disc-shaped or circular hydrophilic insulating paper 28. As can be appreciated, the performance of the electrode sensor is the same, only the location of the electrode 29 is altered from that of the preferred embodiment in FIG. 4.

In summary, improved leak detection for an electromagnetic conduction-type conductivity meter is provided and is particularly valuable where economically manufactured resin housing are utilized and can be subject to cracking during the life of a product. In those cases, 10 sample liquid can enter into the inside of the casing and the entrance of the sample liquid can be detected in an early fashion, thereby preserving the integrity of the measured signals, preventing damage to the coil, and eliminating the potential contamination of the liquid.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved detector assembly of an electro-magnetic induction-type conductivity meter comprising;
    a housing member having a liquid sample flow path extending therethrough;
    an excitation coil mounted in the housing member and extending about and separated from the liquid sample flow path;
    a detection coil mounted in the housing member and extending about and separated from the liquid sample flow path;
    means for providing a second liquid sample flow path that interconnects with the first liquid sample flow path both upstream and downstream of the respective coils, the second liquid sample flow path being adjacent the coils and substantially surrounding the coils, whereby the excitation coil enables an induction current to be generated in the liquid sample and the detection coil measures the induction current as representative of the liquid sample; and
    means for detecting any entrance of the liquid sample into the housing member that would directly contact one of the coils.

2. The detector assembly of claim 1 wherein the means for detecting includes an electrode spaced from one of the coils.

3. The detector assembly of claim 2 wherein the means for detecting further includes an insulating porous paper positioned between the electrode one of the coils.

4. The detector assembly of claim 3 wherein the electrode is porous.

5. The detector assembly of claim 4 wherein the insulating paper is hydrophilic.

6. An improved detector assembly of an electro-magnetic induction-type conductivity meter which can be connected to a pipeline, comprising:
    a two-piece molded housing member unitarily connected together and having a first liquid sample flow path extending therethrough including first and second male coupling projections for connection to a pipeline;
    an excitation coil in the housing member and extending about the first liquid sample flow path;
    a detection coil in the housing member and extending about the first liquid sample flow path;
    means for providing a second liquid sample flow path extending through the housing member that interconnects with the first liquid sample flow path both upstream and downstream of the respective coils, the second liquid sample flow path including a first channel and a second channel that are approximately 180 degrees apart, the second liquid sample flow path being adjacent the coils, whereby the excitation coil enables an induction current to be generated in the liquid sample and the detection coil measures the induction current as representative of the liquid sample; and
    means for detecting the presence of any liquid which enters into the housing member adjacent the respective coils.

* * * * *